US011608892B2

(12) United States Patent
Lopez Ondevilla et al.

(10) Patent No.: US 11,608,892 B2
(45) Date of Patent: Mar. 21, 2023

(54) PLUG, MACHINE AND PROCESSING METHOD UNDER HIGH PRESSURE

(71) Applicant: HIPERBARIC, S.A., Burgos (ES)

(72) Inventors: Raul Lopez Ondevilla, Burgos (ES);
Ruben García Reizabal, Burgos (ES);
Santiago Tarrago Mingo, Burgos (ES);
Andres Felipe Hernando Saiz, Burgos (ES); Wouter Nicolaas Andries Burggraaf, Burgos (ES)

(73) Assignee: HIPERBARIC, S.A., Burgos (ES)

( * ) Notice: Subject to any disclaimer, the term of this patent is extended or adjusted under 35 U.S.C. 154(b) by 409 days.

(21) Appl. No.: 16/645,450

(22) PCT Filed: Sep. 7, 2017

(86) PCT No.: PCT/ES2017/070600
§ 371 (c)(1),
(2) Date: Mar. 6, 2020

(87) PCT Pub. No.: WO2019/048716
PCT Pub. Date: Mar. 14, 2019

(65) Prior Publication Data
US 2020/0284347 A1 Sep. 10, 2020

(51) Int. Cl.
*A61L 2/26* (2006.01)
*F16J 12/00* (2006.01)
(Continued)

(52) U.S. Cl.
CPC ............ *F16J 12/00* (2013.01); *A23L 2/42* (2013.01); *A23L 3/0155* (2013.01); *A61L 2/02* (2013.01);
(Continued)

(58) Field of Classification Search
CPC . A23L 2/42; A23L 3/0155; A61L 2/02; A61L 2/26; A61L 2202/121;
(Continued)

(56) References Cited

U.S. PATENT DOCUMENTS

| | | | |
|---|---|---|---|
| 3,151,650 A | 10/1964 | Beck | |
| 5,993,172 A | 11/1999 | Schuman | |
| 6,305,913 B1 * | 10/2001 | Hashish | F04B 7/0266 92/92 |

FOREIGN PATENT DOCUMENTS

| | | | | |
|---|---|---|---|---|
| EP | 2308325 A1 * | 4/2011 | ........... | A23L 3/0155 |
| WO | WO 00/64493 A3 | 11/2000 | | |

(Continued)

OTHER PUBLICATIONS

English-Language Machine Translation of EP 2308325 (Year: 2011).*

*Primary Examiner* — Timothy C Cleveland
(74) *Attorney, Agent, or Firm* — Don D. Cha; HDC Intellectual Property Law, LLP

(57) ABSTRACT

Plug for high-pressure processing machines with a bag, comprising a duct for the passage of a pressure-transmitting fluid to the bag, another duct for filling and emptying of a product to be pressurized and a valve. The plug is further provided with a rod for opening and closing the valve. Said rod is located in the duct for the product and has its own inner duct joined to a cleaning agent chamber for the passage of the cleaning agent through the product duct. The invention also relates to a machine incorporating said plug and a method for the processing of pumpable substances. Hygienic design and very high pressure sealing requirements are met by the invention.

15 Claims, 5 Drawing Sheets

(51) Int. Cl.
*A23L 2/42* (2006.01)
*A23L 3/015* (2006.01)
*A61L 2/02* (2006.01)
*F16J 13/00* (2006.01)

(52) U.S. Cl.
CPC ................. *A61L 2/26* (2013.01); *F16J 13/00* (2013.01); *A23V 2002/00* (2013.01); *A61L 2202/121* (2013.01); *A61L 2202/122* (2013.01); *A61L 2202/17* (2013.01)

(58) Field of Classification Search
CPC . A61L 2202/122; A61L 2202/17; F16J 12/00; F16J 13/00
See application file for complete search history.

(56) References Cited

FOREIGN PATENT DOCUMENTS

| | | | |
|---|---|---|---|
| WO | WO-0064493 A2 * | 11/2000 | ........... A23L 3/0155 |
| WO | WO 01/13030 A2 | 2/2001 | |
| WO | WO-2007036775 A1 * | 4/2007 | ............... A23B 4/00 |

* cited by examiner

PLUG, MACHINE AND PROCESSING METHOD UNDER HIGH PRESSURE

CROSS-REFERENCE TO RELATED APPLICATIONS

This application is a 35 U.S.C. § 371 U.S. National Stage Application of PCT Patent Application No. PCT/ES2017/070600, filed Sep. 7, 2017, which is incorporated herein by reference in its entirety.

TECHNICAL FIELD

The present invention belongs to the sector of devices and methods for high-pressure processing of substances known as "pumpable" substances, in particular though not limited to fluids such as beverages, cosmetics, etc.

BACKGROUND OF THE INVENTION

High-pressure processing (HPP) is a technology that, at pressures above 4,000 bar, manages to reduce the microbial load, without altering the characteristics of the processed product.

HPP equipment known for treatment of liquids or other substances through high pressure are based on the processing of the product previously arranged in flexible containers, for example in bottles. The classic form of high-pressure processing is carried out in batches, that is, by means of a discrete and non-continuous process. Initially, the products inside their flexible final containers are loaded into rigid plastic containers that are loaded into a steel vessel, which is then filled with water (the remaining space, since there are unoccupied gaps between the containers). Once filled, it is completely closed and the water starts to be pumped at high pressure (through one or more high-pressure intensifiers) up to 4,000-6,000 bar and said pressure is maintained for a time that can vary from a few seconds to several minutes. The pressure reached and the time that it is maintained are the parameters of the process that are defined in each case depending on the product to be processed (this is called "recipe"). For example, in the case of a beverage, the technology is used because of its microorganism inactivation effect and the recipe is defined according to the desired level of microorganism inactivation to be achieved. Finally, the pressure is released, the containers are removed from the interior of the vessel and the processed product is extracted. The product has been sanitized, that is, the microbial load thereof has been reduced.

In an HPP batch process, the pressure is transmitted to the products through the pressurizing fluid, usually water, being a pressure that is transmitted equally and instantaneously to all points of the product. Given that the product is processed when already packaged, the filling coefficient of the vessels (relationship between the product volume to be processed and the useful volume of the vessel) is low, between 40% and 60%, depending on the geometry of the container and the vessel diameter. It can be concluded from all of the above that the main advantage of batch processing is the absence of subsequent contamination of the product, since from the beginning it is in its final packaging. On the other hand, the main disadvantage is that the low filling coefficient that is achieved limits the productivity of the traditional high-pressure processing equipment. Other disadvantages of the batch process are the need to use flexible packaging that can withstand the effect of high pressures (the use of materials such as glass not being possible) as well as handling them for loading and unloading the HPP machine.

Therefore, there is a need to look for an alternative to the current processing mode that can increase the filling coefficient of the vessel and avoid the restrictions on the type of packaging, ensuring that contamination is not produced after the processing of the product, the latter being the most difficult to achieve.

Over time, different solutions have been considered, mainly oriented in two directions: processing liquids directly inside a vessel with a piston that transmits the pressure, or processing liquids inside a bag or flexible membrane located inside the vessel and occupying as much useful space as possible.

In the case of the systems that include a displaceable piston inside the vessel, intended to apply pressure directly, it separates two regions, one that comprises the pumpable product to be treated and another in which the pressure-transmitting fluid (usually water) is found. These systems have the main drawback that the piston requires high-pressure joints specially designed to prevent mixing the liquids of the two areas. Said joints require constant monitoring and substantial maintenance. Furthermore, this solution is not hygienically optimal, since it is very easy for the product, once processed (and thus "sanitized"), to come into contact with contaminated areas (pressure-transmitting fluid) and to undergo contamination.

During the 1990's, several types of equipment were developed that worked by processing the product in bulk (in a semi-continuous system). All of these operated with a piston and had problems of hygiene (difficult cleaning of the equipment and contamination of the product once processed) and problems of mechanical reliability reason for which they are no longer being manufactured.

An example of a system provided with a membrane is found in application U.S. Pat. No. 5,993,172A. However, this system does not have good hygienic conditions, since it does not prevent the contamination of the product that has been processed or that is being processed due to the exposure/passage thereof to a duct that is not correctly sanitized, since the design was not conceived to be easy to clean.

Other solutions that have been proposed for this type of high-pressure processing equipment include very complex systems with a large number of valves, pipes and joints subjected to high pressure that, apart from being difficult to clean, are susceptible to having reliability problems due to the complexity thereof. It is known that equipment working at very high pressure require elevated maintenance, so in order to increase productivity and reduce machine downtime, it is essential to have a simple and efficient design in which the number of components, valves, tubes, couplings and joints subjected to high pressure is kept as low as possible.

SUMMARY OF THE INVENTION

The object of the present invention is that of providing a plug for a high-pressure processing machine that resolves the aforementioned drawbacks, which will enable processing pumpable substances in a flexible bag located inside the vessel. In particular, said plug meets the requirements of hygienic design and sealing at very high pressure, enabling the cleaning of its inner ducts, which guarantees the absence of contamination of the processed product that must pass through said ducts at the end of the process. The plug is located at one end of a machine having a high-pressure vessel and enables filling and emptying of a flexible bag (located inside), in which the product of interest is pressurized. It comprises a duct for the passage a pressure-transmitting fluid, another duct for the inlet and outlet of product to be processed in the bag and a seat valve with a male and a female seat in order to enable or prevent the passage of the product to or from the bag. A rod joined to the male seat and usually actuated by an actuator is located inside the filling/emptying duct in order to close and open the valve. The rod has an inner duct joined to a cleaning agent chamber such that while the product is being processed inside the bag, the filling/emptying duct remains under a bath of cleaning agent.

The invention also relates to a high-pressure processing machine (1,000-10,000 bar) including said plug and a pressurization method by means of said machine. The machine thus conceived, which would achieve an elevated filling coefficient of up to 90-95% would meet the objective of inactivating the microorganisms and/or modifying properties of perishable liquid/pumpable products (such as beverages, food, cosmetic/pharmaceutical products, etc.) maintaining hygiene at all points of the machine and the process.

DESCRIPTION OF THE FIGURES

In order to assist in a better understanding of the characteristics of the invention, this description is accompanied by the following figures, as an integral part thereof, which by way of illustration and not limitation represent the following.

DETAILED DESCRIPTION

Figure 1:
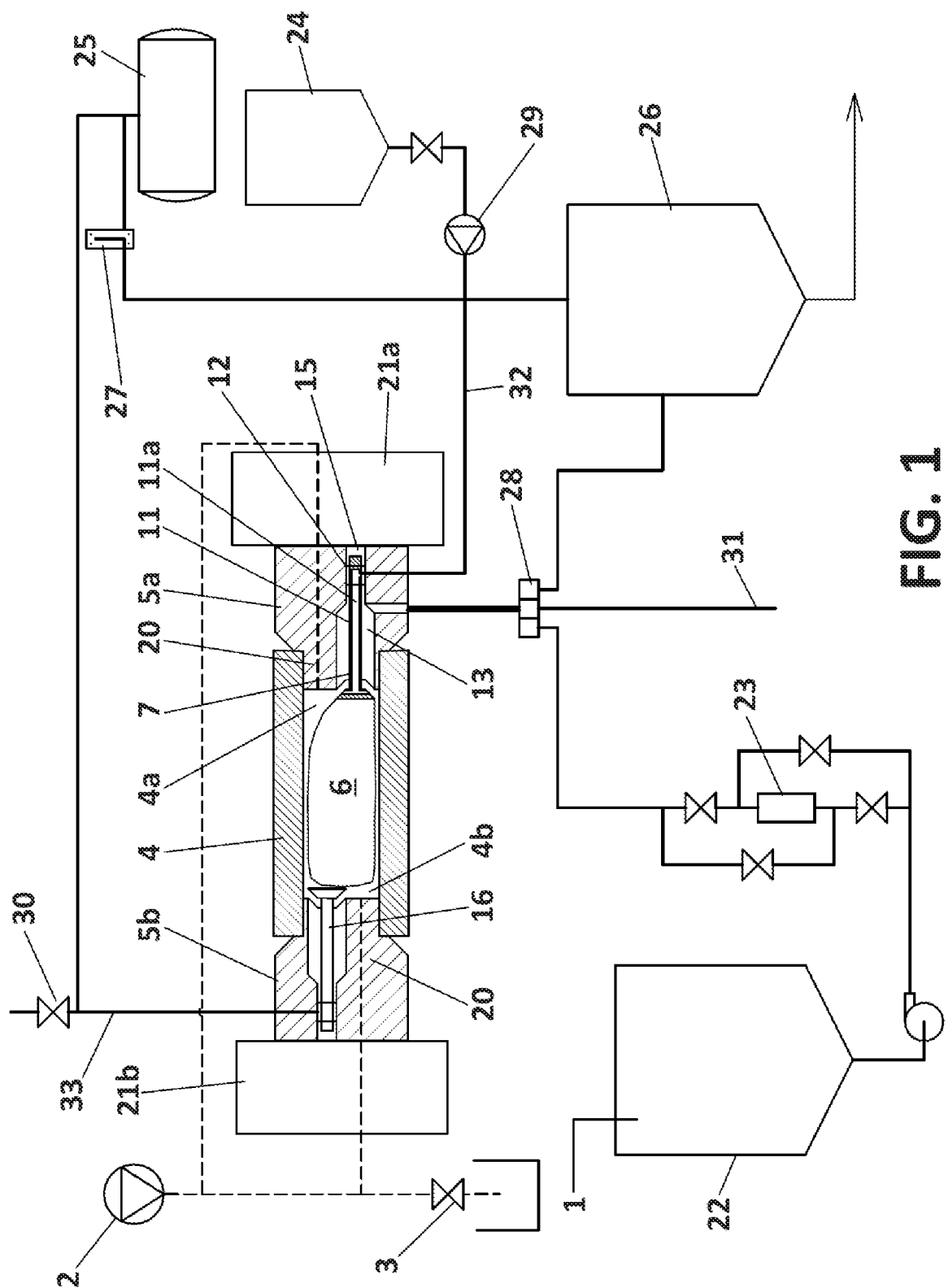
FIG. 1 is a schematic view of the high-pressure processing machine incorporating the plug of the invention.

FIG. 1 shows the diagram of a machine incorporating the plug of the invention. It comprises a source of a product to be pressurized 1, which is temporarily stored in a tank 22 and is transferred through a circuit of pipes and through the product plug 5a to a flexible bag 6 situated inside a high-pressure vessel 4 provided with two openings at the ends 4a and 4b. Once the flexible bag is filled with product, a pressure transmitting fluid, generally water, is introduced into the vessel, through two plugs 5a and 5b, by means of one or more pumps 2 and through the ducts provided for this purpose in both plugs 20. The fluid will exert the pressure defined in the process (around 6,000 bar for most recipes). The pressure will be maintained for a certain amount of time and once the process has ended, one or more discharge valves 3 will cause the pressure inside the vessel 4 to be reduced to atmospheric pressure. The product plug 5a, which is the invention itself, separates the area in which high-pressure processing takes place from the area that must always be sanitized, since once the product has been "sanitized" (processed and therefore free from microorganisms) it leaves the flexible bag through the same duct through which it entered unprocessed (and therefore possibly initially contaminated with microorganisms) and the absence of contamination must be guaranteed in this phase.

Figure 2:
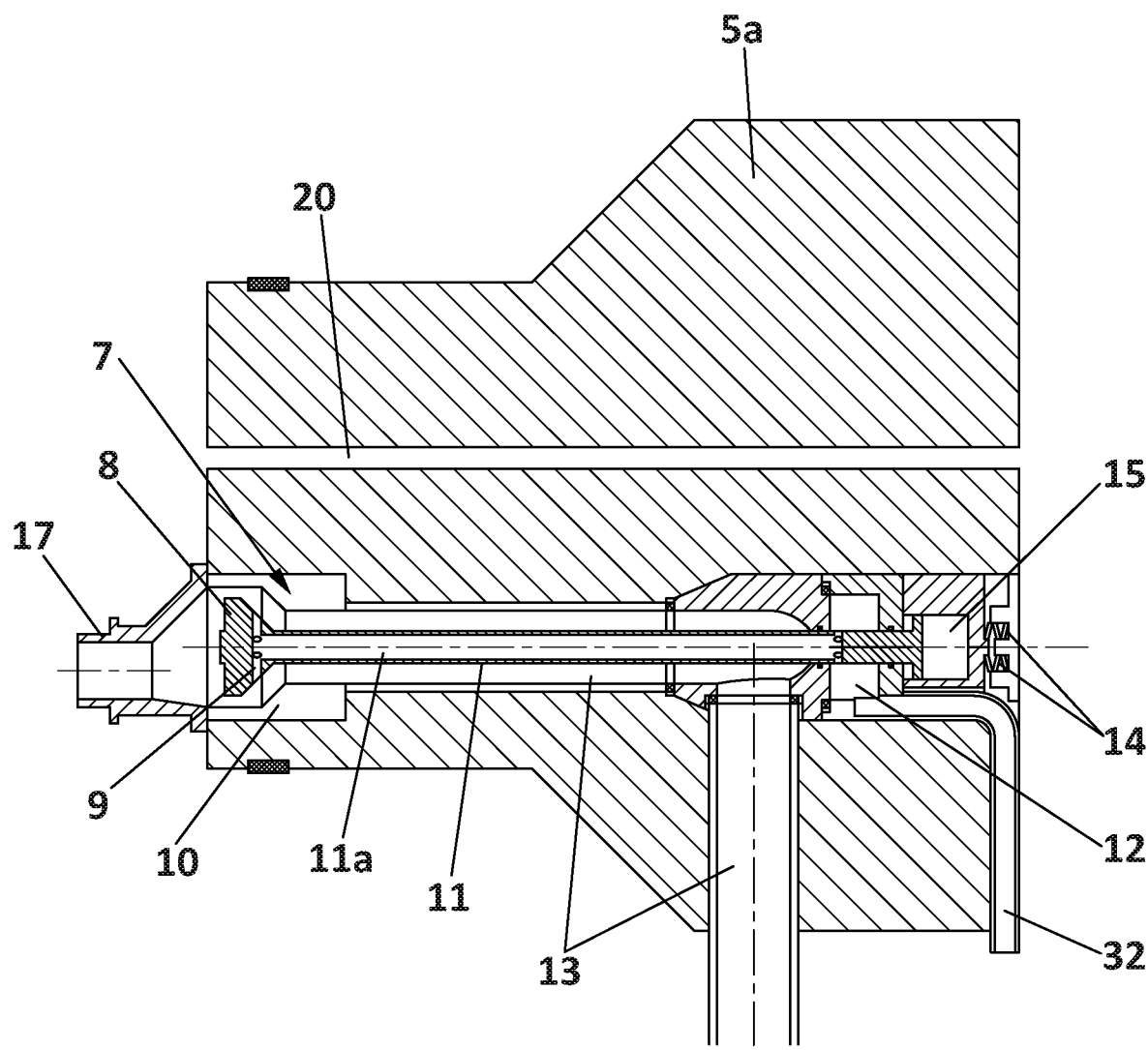
FIG. 2 shows the plug of the invention (product plug).

In reference to FIG. 2, the plug of the invention 5a has an inner filling and emptying duct 13 for the product to be pressurized, in addition to the duct for the pressure transmitting fluid 20. A seat valve 7 at the end of the plug in contact with the bag 6 prevents the filling and emptying duct 13 from being subjected to high pressure during the HPP cycle (all the phases of the high-pressure processing). The existence of this valve means that the filling duct, which is the same duct as for emptying, can be designed with a hygienic design standard and is consequently easy to clean effectively during the phase of maintained pressure of the HPP cycle.

Figure 3:
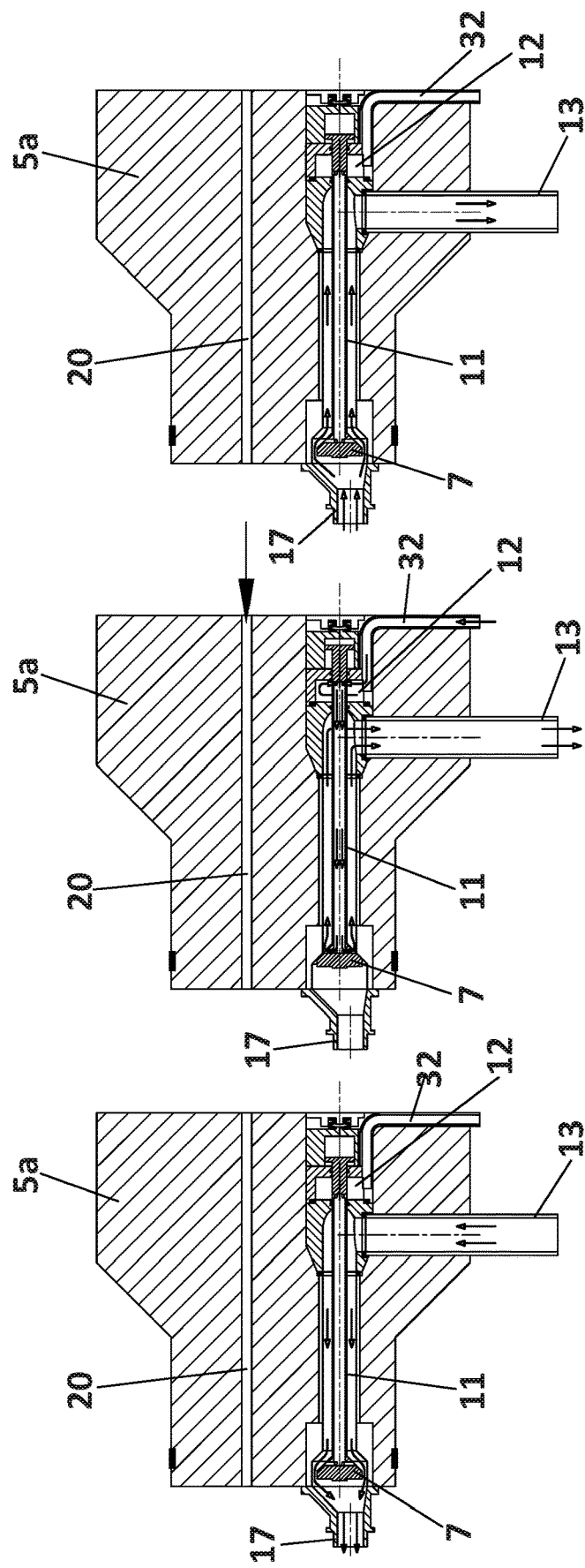
FIGS. 3a-3c show the product plug during the steps of filling and emptying the bag and cleaning the duct.

The valve 7 consists of a male seat 8 and a female seat 10, both of which are manufactured from a corrosion-resistant material with an elastic limit greater than 600 MPa, in order to withstand pressures greater than 6000 bar, such as for example 15-5PH H900 or 13.8Mo H1000 steel. The angle of the seat is between 60° and 100°. The closing and opening of the valve 7 is produced by means of the translation of a rod 11 by means of an actuator 15, which may be hydraulic. The rod is directly connected to the male seat 8 of the valve. Thus, a simple movement in the direction of the shaft of the plug and the machine produces the closing (FIG. 3b) or the opening of the valve (FIGS. 3a and 3c). As it is a metal-to-metal seal, the use of high-pressure joints in contact with the liquid to be treated is avoided because they are very difficult to clean and can be a source of accumulation of organic matter, and therefore microorganisms, if they do not have a hygienic design, something very complicated if they are to withstand high pressure. This valve is easy to clean and is also very reliable and simple from a mechanical point of view. It separates the area that is subjected to high pressure from the one that must have a hygienic design.

In order to fill the bag with a product to be processed, the valve 7 of the plug 5a is opened (FIG. 3a). The product is in a tank 22 and is transferred through a three-way valve 28 to the inner filling and emptying duct 13 of the plug. Optionally, the product is passed through a filter 23 in case it is necessary to eliminate seeds, pulp or other particles, which helps to prevent any solid particles from remaining in the valve seats that could damage the sealing capacity, since the filtered product sweeps and cleans said particles. Once the bag 6 is full, the actuator moves the rod 11 and the valve closes (FIG. 3b). A tank with cleaning agent 24 (peroxide, steam or another compound with disinfecting action) is then opened, located on the outside of the vessel. The cleaning agent enters the plug by means of a pump 29 and, through a duct 32 in the product plug, reaches a chamber 12 and the rod 11. The rod 11 has holes and a duct 11a therein such that the cleaning agent enters through the holes and flows through the interior of the rod to the end where the male seat 8 is located, exiting through it through other holes. In this way, the inner product filling/emptying duct 13 is cleaned and the agent returns towards the outer three-way valve 28, which leads it to a drain 31. The chamber 12 at the end of the duct 32, through which the cleaning agent enters, is long enough to maintain the portion of the rod 11 that enters the duct 13 clean when the valve opens. Thus, the portion of the rod entering into the clean area is kept continuously in a bath of cleaning agent in order to ensure hygiene thereof when the valve is actuated.

The components of the duct 13 are preferably manufactured from austenitic stainless steel. These materials have high resistance to corrosion when exposed to certain liquid substances such as juices or other low-pH foods. This duct 13 helps to protect the structural material of the plug since it prevents direct contact thereof with the product to be pressurized. The plug is preferably made of stainless steels with an elastic limit greater than 900 MPa, preferably greater than 1000 MPa, which have lower resistance to corrosion than austenitic steels.

The different portions of the duct 13 are joined by means of hygienic joints on which it is necessary to maintain a certain tension in order to ensure tightness. Furthermore, the plug undergoes deformations under pressure that cannot be absorbed by the elements 13, 12 and 15 without the inclusion of an elastic element such as springs or an elastomer. The elastic elements 14 positioned at the distal end of the plug (end furthest from the bag) absorb the deformations of the plug due to the pressure and also maintain at all times the hygienic joints of the duct 13 with the tension necessary to ensure tightness.

Figure 4:
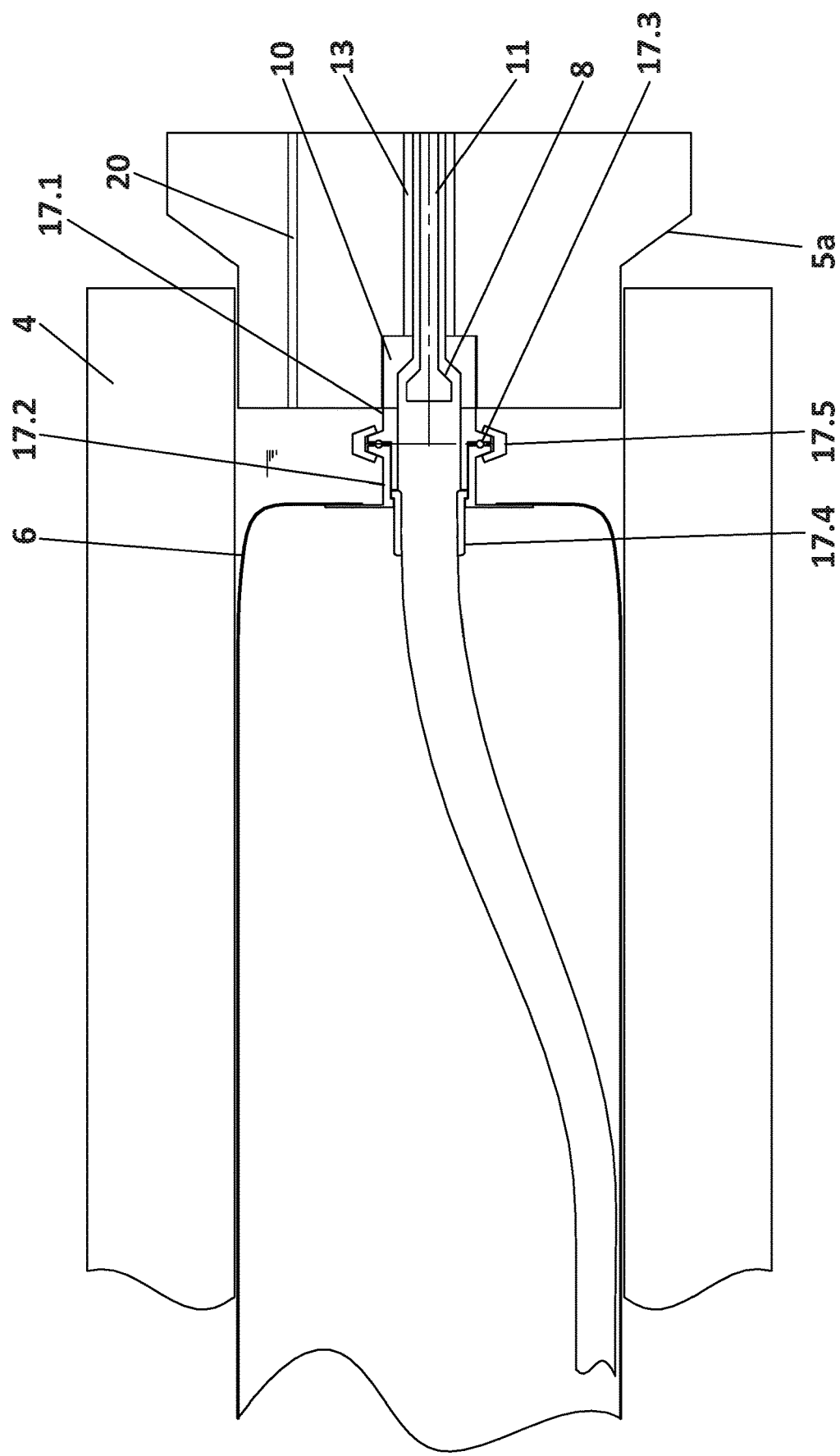
FIG. 4 is a detail of the anchoring system of the bag to the plug.

At the end of the plug there is a connector 17 (FIG. 3 and FIG. 4) adapted to connect the flexible bag 6. This connection enables the filling and emptying of product from the bag 6 in a hygienic manner and in turn guarantees that throughout the high-pressure processing, the product to be processed is isolated from the pressure-transmitting fluid. The bag 6 is provided with a flexible female connector 17.2 attached thereto. The connector 17.2 joins a male connector 17.1 attached to the plug, by means of a joining flange 17.5 preferably made of plastic material and a fastening part 17.4 to which a hose, pipe or another system can be connected in order to facilitate emptying the bag. The male connector 17.1 in turn is in contact with the female seat 10 and the latter, in turn, is in contact with the inner filling/emptying duct 13. The parts 17.1, 10 and 13 may in some cases be one single part. Optionally, an elastomeric joint 17.3 is placed between the male 17.1 and female 17.2 connectors in order to ensure tightness in the phases of the cycle in which there is no high pressure outside the bag, that is, during the product filling phase of the bag and during the extraction phase of the treated product from the bag. This joint 17.3 receives the sealing pressure necessary in order confer tightness to the connection. As the pressure of the transmitting fluid increases, all the parts that make up the joint start to reduce their volume as a result of the effect thereof. Due to the different module of compressibility between steel and plastic, the connector 17.2 of the bag is increasingly compressed against the male connector 17.1 of the plug which, being metallic, barely reduces its volume, achieving a plastic-metal seal. The elastomeric joint 17.3 is likewise compressed by recovering its volume in the depressurization and therefore the closing function thereof.

Figure 5:
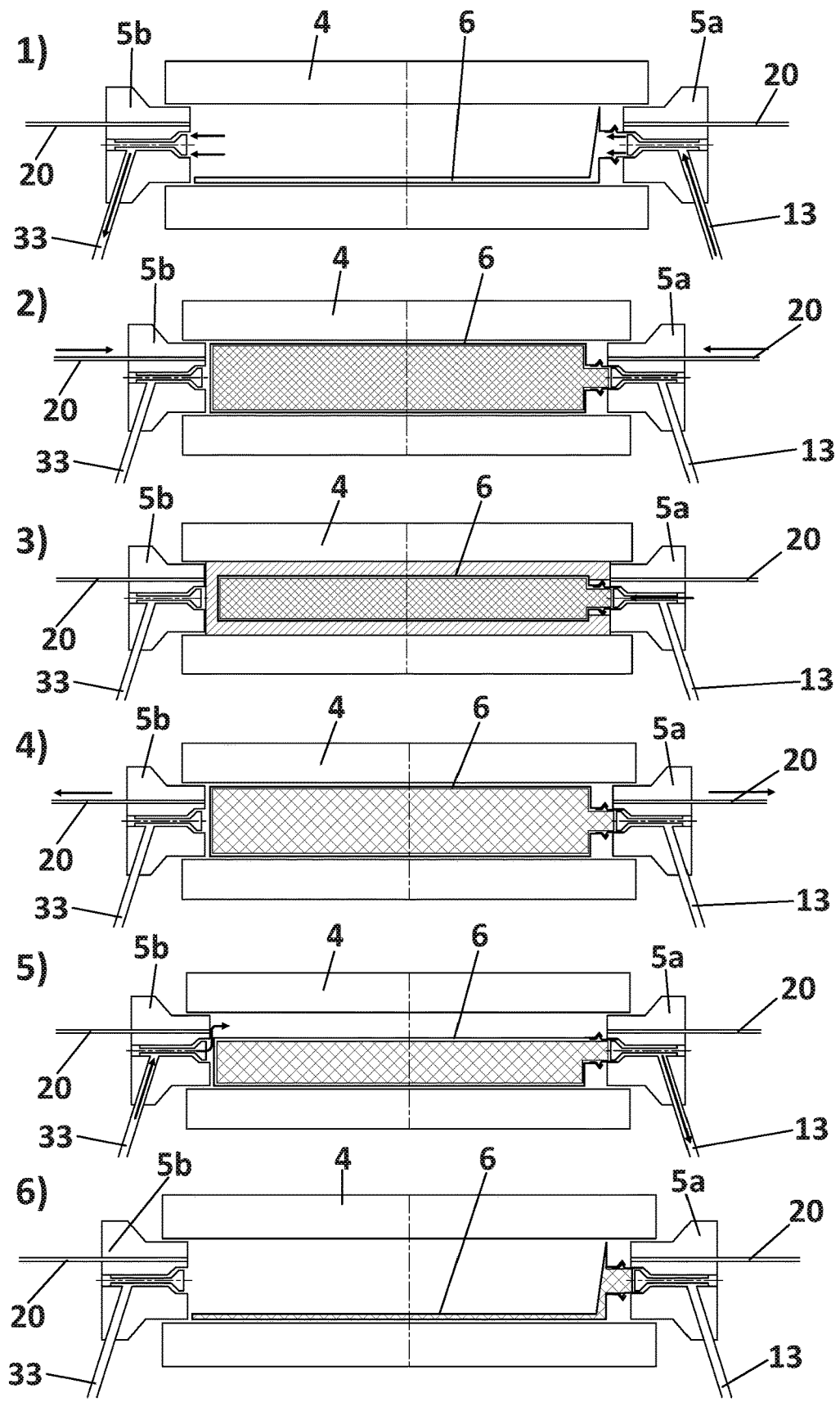
FIG. 5 shows a transverse cross section of the plugging elements, vessel and bag during the different steps of the processing method carried out with the machine.

In reference to FIGS. 1 and 5, the method of pressurizing the product to be treated is as follows:

In order to place the bag 6 into the vessel 4, the machine is provided with two wedges 21a, 21b that can be displaced laterally in a direction perpendicular to the main axis of the machine. Removing the wedges makes it possible to remove the plugs 5a, 5b and access the vessel. The vessel 4 is then moved transversally so that it stays outside the yoke that supports all the elements (not shown in the figure), so that access to it is achieved. Once the bag 6 is introduced, the vessel 4 is again moved transversally, recovering the alignment thereof with the yoke. The connection between the bag 6 and the product plug 5a is then carried out. Subsequently, the plugs 5a, 5b are again introduced into the vessel and the wedges 21a, 21b recover the initial position thereof. The product to be processed is then introduced through the duct 13 of the product plug (FIG. 5.1). The air present in the vessel 4 exits through the plug on the opposite side 5b through the duct 33 through the opening of the aeration valve 16 and is expelled into the atmosphere through the valve 30. Then (FIG. 5.2), the pressure-transmitting fluid is introduced into the vessel by means of the pump (or pumps) 2 through the ducts 20 present in both plugs 5a, 5b. The pressure increases to the chosen recipe pressure, normally between 4,000 and 6,000 bar, and is maintained for a predetermined period of time (FIG. 5.3), which is also defined by the recipe and adapted in each case to the product (liquid) to be processed. During this process (raising and maintenance of pressure) the product plug 5a is cleaned as described in reference to FIG. 3b. The cleaning agent is in a tank 24 and is brought into a chamber 12 by means of a pump 29 through the duct 32. Once the duct has been cleaned, the cleaning agent is discharged through the duct 13 to the three-way valve that empties it into a drainage duct 31. Once the pressure has been maintained for a set period of time and the product has been processed, a portion of the transmitting fluid introduced during the raise in pressure leaves the vessel through ducts 20, due to the actuation of the relief valve or valves 3 (FIG. 5.4) until the atmospheric pressure is reached. The actuator 15 then opens the valve 7 and the bag 6 starts to discharge with the help of pressurized air or inert gas, which reaches the vessel, pressing on the outside of the bag, through the duct 33 of the aeration plug 5b from a tank 25 (FIG. 5.5) upon opening the aeration valve 16. The pressure of the air or inert gas acts on the outside of the flexible bag 6, facilitating the emptying thereof, making the product pass, through the connector 17, through the duct 13 of the plug 5a to the processed product tank 26 through the valve 28. Finally, the entire processed product remains in the tank 26 and the bag empties (FIG. 5.6). Once the transfer of the processed product to the tank 26 has been completed, the pressure of the remaining air or gas in the vessel 4 is released through the valve 30, leaving the equipment ready to start of a new processing cycle, changing the bag 6 if necessary. The new processing cycle would begin by introducing new product to be processed (FIG. 5.1), and it is not necessary to carry out machine movements if the bag 6 is not changed, an action that is not carried out in every cycle. Once the product of the tank 26 is confirmed as suitable, it is transferred to the filling or storing equipment, propelled by air or inert gas proceeding from the tank 25 and filtered through a sterile filter 27 to avoid possible contamination of the product.

Thanks to the product plug, the filling/emptying duct with the product to be processed is not subjected to high pressure, so that the cleaning of said duct with a cleaning agent (such as steam or peroxide) is easier, since easily cleaned joints and corrosion-resistant materials can be used in the design thereof. Furthermore, it prevents the complicated pipes, couplings and valves in contact with the fluid to be treated from being subjected to fatigue, due to the high pressure and therefore cause cleaning problems due to the growth of microorganisms inside cracks.

The invention, in comparison with other previous solutions, is mechanically simple, such that from a mechanical reliability point of view it is robust, the areas subjected to high pressure being as small as possible. Thanks to the invention, which clearly separates the areas that must have a hygienic design from those that must be designed to withstand high pressure, hygienic and mechanical reliability are high. Furthermore, the two areas are separated by a metal-to-metal seal that is easy to clean and significantly reliable from a mechanical point of view. The liquid to be treated is prevented from being pressurized in the areas with elastomeric joints where it is necessary to carry out high-pressure sealing, the high-pressure supporting design of which does not make them easy to clean or suitable from a hygienic point of view. It also prevents the pipes from being subjected to high pressure by means of the fluid to be treated, which could generate fatigue cracks where microorganisms could develop, the cleaning thereof being very complicated and it enables the use of corrosion resistant materials.

In view of this description and the figures, the person skilled in the art will understand that the invention has been described according to certain preferred embodiments thereof, but that multiple variations may be introduced into said preferred embodiments without exceeding the object of the invention as has been claimed.

The invention claimed is:

1. A high-pressure processing machine comprising a vessel (4), a means for pressurizing (2) and depressurizing (3) said vessel (4), an aeration plug (5b), a bag (6) and a product plug (5a), wherein the product plug (5a) comprises a duct for the passage of a pressure-transmitting fluid (20), a product filling and emptying duct (13) for filling and emptying with a product to be pressurized in the bag (6) and a seat valve (7) with a male seat (8) and a female seat (10) in order to enable or prevent the passage of the product into the bag (6), the plug being provided with a rod (11) on the inside of said product filling and emptying duct (13) for closing and opening the valve (7), wherein the rod (11) is joined to the male seat (8) and is provided with an inner duct (11a) joined to a cleaning agent chamber (12), which in turn is joined to an inlet duct of a cleaning agent (32) and wherein the rod (11) and the male seat (8) are provided with holes for the passage thereof, wherein said machine fills and empties said product through said product filling and emptying duct (13), and wherein said processed product is absent of contamination after being removed through said filling and emptying duct (13).

2. The high-pressure processing machine according to claim 1 wherein an angle of the seat valve (7) is between 60° and 100°.

3. The high-pressure processing machine according to claim 1 further comprising an actuator (15) adapted to actuate the rod in order to open or close the valve (7).

4. The high-pressure processing machine according to claim 1, wherein the valve is made from a material that comprises stainless steel.

5. The high-pressure processing machine according to claim 1, wherein the product filling and emptying duct (13) is made up of different austenitic stainless steel parts joined by hygienic joints, the plug comprising stainless steels with an elastic limit greater than 900 MPa.

6. The high-pressure processing machine according to claim 1, wherein the product filling and emptying plug (5a) further comprises elastic elements (14) at a distal end thereof.

7. The high-pressure processing machine according to claim 1, wherein the bag (6) and the plug (5a) are joined by means of a connector 17.

8. The high-pressure processing machine according to claim 7 wherein the connector (17) is provided with a female connector (17.2) attached to the flexible bag (6) and a male connector (17.1) joined to the plug (5a), both connectors being joined by means of a joining flange (17.5).

9. The high-pressure processing machine according to claim 8 wherein the connector (17) is further provided, on the side of the male connector (17.1), with a fastening part (17.4) adapted to be connected to a hose or tube in order to facilitate emptying the bag (6).

10. The high-pressure processing machine according to claim 8 further comprising an elastomeric joint (17.3) between the male connector (17.1) and the female connector (17.2).

11. The high-pressure processing machine according to claim 1, further comprising a tank for a cleaning agent (24), means for pumping (29) said agent towards the product plug (5a) through the product filling and emptying duct (13) and means for recovering it from said duct.

12. The high-pressure processing machine according to claim 11 wherein said means for recovering the agent are a three-way valve (28) and a drainage duct (31).

13. The high-pressure processing machine according to claim 1, wherein the aeration plug (5b) is provided with an aeration duct (33) connected to an air tank (25) in order to assist in emptying the bag (6).

14. The high-pressure processing machine according to claim 1 further comprising a tank (26) for the processed product, a tank for air or inert gas (25), a sterile filter (27) for the air or inert gas and means for transferring the processed product from the tank (26) to filling or storing equipment with help of filtered air or inert gas.

15. A method for the processing of pumpable substances using a high-pressure processing machine of claim 1, said method comprising:

pumping a cleaning product from a tank (24) to a chamber (12) in a plug and pumping the cleaning product back so that the cleaning product first flows through an inside of a rod (11a) to a male seat (8) of a valve and exits the valve through holes, and returning through the product filling and emptying duct (13), during a high-pressure processing step and during a time that said high-pressure is maintained.

* * * * *